United States Patent
Ohzawa

(10) Patent No.: US 8,687,928 B2
(45) Date of Patent: Apr. 1, 2014

(54) OPTICAL CHARACTERISTIC MEASURING PROBE

(75) Inventor: Soh Ohzawa, Toyonaka (JP)

(73) Assignee: Konica Minolta Opto, Inc., Tokyo (JP)

( * ) Notice: Subject to any disclaimer, the term of this patent is extended or adjusted under 35 U.S.C. 154(b) by 24 days.

(21) Appl. No.: 13/318,998

(22) PCT Filed: Mar. 3, 2010

(86) PCT No.: PCT/JP2010/053412
§ 371 (c)(1),
(2), (4) Date: Nov. 4, 2011

(87) PCT Pub. No.: WO2010/128605
PCT Pub. Date: Nov. 11, 2010

(65) Prior Publication Data
US 2012/0057149 A1 Mar. 8, 2012

(30) Foreign Application Priority Data
May 7, 2009 (JP) .................................. 2009-112486

(51) Int. Cl.
*G02B 6/26* (2006.01)
*G02B 6/42* (2006.01)

(52) U.S. Cl.
USPC ................................ 385/32; 385/12; 385/117

(58) Field of Classification Search
USPC ........... 385/25, 12, 13, 32, 68, 102, 109, 117, 385/118
See application file for complete search history.

(56) References Cited

U.S. PATENT DOCUMENTS 4,696,544 A * 9/1987 Costella ...................... 385/118

FOREIGN PATENT DOCUMENTS

| JP | 59-195205 | 11/1984 |
|----|-----------|---------|
| JP | 2006-520244 | 9/2006 |
| JP | 2008-89349 | 4/2008 |
| JP | 2008-177697 | 7/2008 |
| JP | 2008-191021 | 8/2008 |
| JP | 4-836820 | 12/2011 |

* cited by examiner

*Primary Examiner* — Charlie Peng
*Assistant Examiner* — Mary El Shammaa
(74) *Attorney, Agent, or Firm* — Cozen O'Connor

(57) ABSTRACT

Provided is an optical characteristic measuring probe which can detect the position and the direction of the leading end of the probe without affecting a monitoring image. The bendable optical characteristic measuring probe is provided with a light guide body (71), which transmits light emitted from a light source and irradiates a subject to be measured with light, and a guide tube (70), which holds the light guide body (71) such that the light guide body freely rotates about the axis and is freely displaced in the axis direction. The light guide body (71) guides at least two types of light, i.e., measuring light for measuring the optical characteristics of the subject to be measured, and position determining light for measuring the position of the light guide body. On the side surface of the guide tube (70), a mark (M) having the characteristics of transmitting the measuring light and returning only the position determining light to the light guide body is provided.

6 Claims, 2 Drawing Sheets

OPTICAL CHARACTERISTIC MEASURING PROBE

This is a U.S. National Phase under 35 U.S.C. §371 of International Application No. PCT/JP2010/05341, filed on Mar. 3, 2010, and claims priority on Japanese application No. 2009-112486 filed on May 7, 2009, the entire content of which is hereby incorporated by reference.

TECHNICAL FIELD

The present invention relates to an optical characteristic measuring probe which is suitable to, for example, an optical coherent tomography (OCT: Optical Coherent Tomography) device, and is provided for irradiating a subject to be measured with light and receiving light returning from a subject to be measured.

BACKGROUND ART

In recent years, for diagnosis of biomedical tissue, there has been proposed an optical coherent tomography (OCT: Optical Coherent Tomography) device which can obtain optical information of the inside of tissue, other than an imaging device which can obtain information of a surface condition of the tissue. An optical coherent tomography device is a technology that low coherence light is divided into two beams, one of the beams is projected to a subject, back scattered light on which phase information of the subject has been given interferes with the other beam, the phase information of the subject is obtained based on intensity information of the inferring light, and an image of a measuring portion of the subject is formed (see Patent Literatures 1 and 2, for example).

In Patent Literature 1, for the purpose of making a penetration catheter penetrate a proper position, a mark is provided on an area of an optical probe of an optical coherent tomography device and the image of the mark is observed, which enables to adjust the position and/or rotation direction of the leading end of the probe.

Patent Literature 2 provides an intraluminal image forming device which uses a probe for being inserted into a lumen to obtain a tomographic image, for observing the inside of the lumen and taking its image with moving the probe in a guide tube. In the intraluminal image forming device, a mark is provided on the guide tube to determine a reference position of a tomographic image, and imaging process is performed without image displacement.

CITATION LIST

Patent Literature

Patent document 1: Japanese Translation of PCT International Application Publication No. 2006-520244
Patent document 2: Japanese Unexamined Patent Application Publication No. 2007-7410

SUMMARY OF INVENTION

Technical Problem

When plural points in a subject to be measured in a body are measured by using an optical probe with a small diameter, it is important that the direction and position of a leading end of the probe are accurately obtained for each measurement. However, since, in the case of a bendable probe, a twist can be given in an area between the leading end and the terminal of the catheter, the accurate position and direction of the leading end of the probe are hardly determined only by the position and the direction of the terminal of the probe.

Further, in the conventional art, the position of the leading end of the probe is determined by arranging a mark for determining the position of the leading end of the probe and by detecting back light which has been generated when measurement light enters the mark and returns. However, since the reference mark is detected by using an actual measurement light, the mark appears in an observed image, which cause problems that shadow of the mark is generated therein, the observed image located behind the mark is shaded and missed, and contrast of the image is deteriorated.

An object of the present invention is to provide an optical characteristic measuring probe which can detect the position and the direction of the leading end of the probe without affecting an observed image.

Solution to Problem

To achieve the above object, the present invention provides an optical characteristic probe which is bendable. The optical characteristic measuring probe is characterized by comprising: a light guide body for transmitting light from a light source and irradiating a subject to be measured with light; and a guide tube for holding the light guide body such that the light guide body freely rotates on an axis of the guide tube and is freely displaced in a direction of the axis, wherein the light guide body guides at least two types of light including measuring light for measuring an optical characteristic of the subject to be measured and position determining light for measuring a position of the light guide body, and a mark is arranged on a side surface of the guide tube, where the mark has a characteristic of transmitting the measuring light and returning only the position determining light to the light guide body.

In the present invention, it is preferable that the measuring light is near infrared light and the position determining light is visible light.

In the present invention, it is preferable that the measuring light is coherent light and the position determining light is incoherent light.

In the present invention, it is preferable that the optical characteristic measuring probe is a rotary scanning probe.

Advantageous Effect of the Invention

According to the present invention, the light guide body transmits two types of light of measuring light and position determining light, and a mark is arranged at a measuring position of the guide tube, where the mark has the characteristics of transmitting the measuring light and returning only the position determining light to the light guide body. Thereby, the position and the direction of the leading end of the probe can be detected by using the position determining light, without affecting an observed image which is observed by using the measuring light.

DESCRIPTION OF EMBODIMENTS

Figure 1:
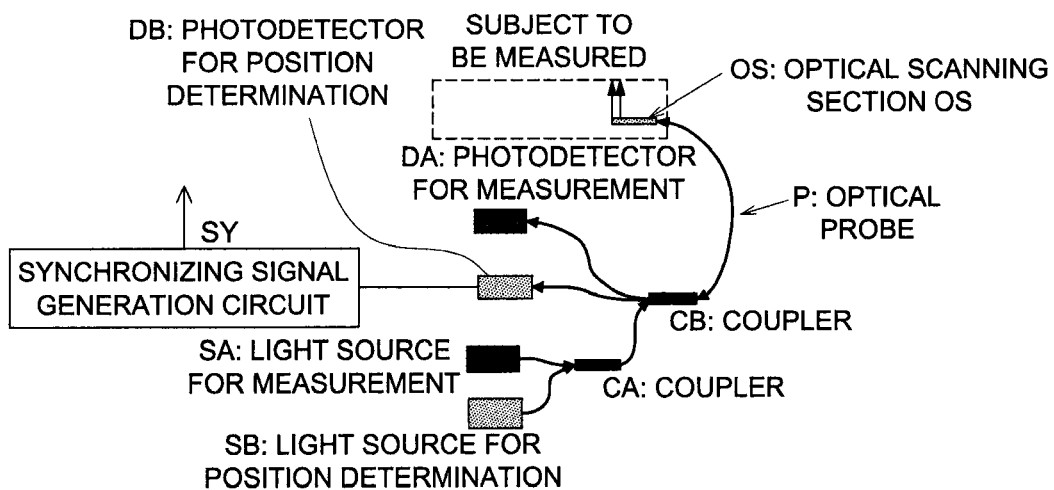
FIG. 1 is a schematic structural view illustrating a concept of the present invention.

FIG. 1 shows a schematic structural view illustrating the concept of the present invention. Optical probe P includes a light guide body such as an optical fiber therein, and optical scanning section OS is arranged on the leading end of the light guide body. Optical scanning section OS irradiates a subject to be measured with light and takes light which has been reflected on the subject to be measured therein.

Light source for measurement SA supplies measuring light for measuring the optical characteristics of the subject to be measured. Light source for position determination SB supplies position determining light for measuring the position of the light guide body. Measuring light and position determining light from light sources SA and SB are coupled together with coupler CA, and are supplied to optical probe P through coupler CB.

In the case of optical coherent tomography (OCT), it is preferable that the measuring light is coherent light in the near-infrared area (for example, wavelength area from 800 nm to 1500 nm) and the position determining light is incoherent light in the visible area (for example, wavelength area from 380 nm to 750 nm). Since the position determining light is incoherent light such as LED light, signal change coming from interference caused when an optical path length changes, which is caused under the condition that the light is coherent light, can be reduced and the position can be measured more accurately.

On the other hand, light which has been reflected on the subject to be measured goes back in optical probe P, and is divided into measuring light and position determining light by coupler CB. Then, the two types of light are detected by photodetector for measuring light DA and photodetector for position determining light DB, respectively. Coupler CB is an optical element which transmits measuring light and position determining light from light sources SA and SB and separates light going back from optical probe P into measuring light and position determining light depending on wavelength.

Signal from photodetector for measuring light DA is used for measuring optical characteristics of the subject to be measured. Signal from photodetector for position determining light DB is supplied to synchronizing signal generation circuit SY and is converted into synchronizing signal for optical scanning section OS.

Concretely, a circulator, wavelength-selective filter (for example, dichroic filter) and WDM (wavelength division multiplexing) device can be used for couplers CA and CB.

Figure 2:
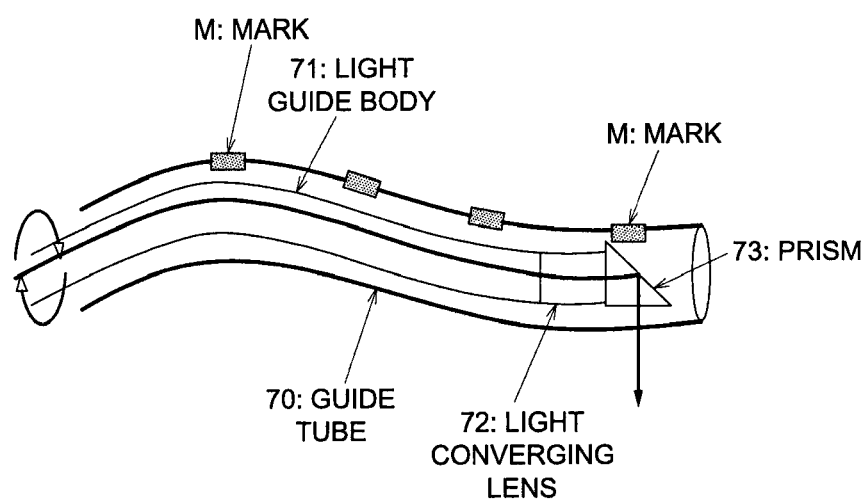
FIG. 2 is a structural view showing an example of an optical probe relating to the present invention.
Each of FIGS. 3a and 3b is a sectional view showing various structures around the leading end of the optical probe.
Figure 3A:
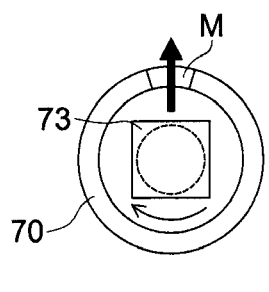
Figure 3B:
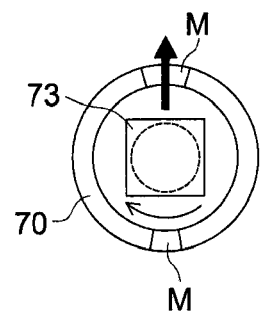

FIG. 2 is a structural view showing an example of an optical probe relating to the present invention. Each of FIGS. 3a and 3b is a sectional view showing various structures around the leading end of the optical probe. The optical probe is composed of guide tube 70, light guide body 71, light converging lens 72 and prism 72, and is structured to be bendable as the total system.

Guide tube 70 has an sectional shape forming a circular cylinder, and is formed of an elastic material with high transmittance for measuring light, for example, fluoroethylene resin. Light guide body 71 is formed of an elastic material with high transmittance for the measuring light and position determining light, for example, an optical fiber. Light guide body 71 is housed inside guide tube 70 and is held such that the light guide body freely rotates on its axis and is freely displaced in the axis direction. A rotating drive mechanism is arranged on the base of the light guide body 71, and the light guide body 71 is structured such that light guide body 71 can rotate on the axis at a constant rotation speed, for example, 1200 rpm.

Light converging lens 72 is mounted on the leading end of light guide body 71. Prism 73 includes a reflection surface for reflecting the measuring light and position determining light, and is mounted on light converging lens 72. Light converging lens 72 and prism 73 rotate together with light guide body 71 as one body and emit the measuring light and position determining light in the radial direction to carry out rotation scanning of the subject to be measured throughout 360 degrees, where the subject is located outside guide tube 70.

In the present embodiment, mark M is arranged on the side surface of guide tube 70, where the mark M has the characteristics of transmitting the measuring light and returning only the position determining light to light guide body 71. It is preferable that such the mark M exhibits the same optical characteristics as guide tube 70 with respect to the measuring light, and further exhibits the optical characteristics different from guide tube 70 with respect to the position determining light. For example, a material or coating whose light transmittance, light scattering characteristic and light reflectance change depending on wavelength is selected.

For example, mark M can be formed to scatter only the position determining light. When the measuring light is infrared light and the position determining light is visible light, mixing microparticles with the size of wavelength of the position determining light therein, can provide a structure that the position determining light is greatly scattered and infrared light whose wavelength is longer than the position determining light is not sufficiently scattered. In this case, the wavelengths of the position determining light and the measuring light are required to be set to have sufficiently different values.

Alternatively, a film having a reflectance which changes depending on wavelength can be formed as the mark M, which can achieve the similar effect as the above structure, when it reflects light with wavelength of the position determining light and transmits light with wavelength of the measuring light.

Such the mark M can be formed with referring to a bandpass filter disclosed in Japanese Unexamined Patent Application Publication No. S58-31307, and a multi-layer mirror which reflects only light in the visible area and is disclosed in Japanese Unexamined Patent Application Publication No. S59-195205.

Further, a reflective volume grating can be used. When the measuring light is infrared light with wavelength of about 800 nm, the grating may have a pitch being half or less of the wavelength, for example, being a value in the range from 200 nm to 400 nm. Such the grating can transmit infrared light and can reflect visible light.

Mark M may be formed by being replaced with a part of the wall surface of guide tube 70, as shown in FIG. 3a and FIG. 3b, or may be formed as a coating film on the outer surface or inner surface of guide tube 70.

FIG. 3a shows an example that one mark M is formed in a scanning area of 360 degrees. When prism 73 rotates and light is projected toward an area of guide tube 70 where mark M does not exist, the measuring light passes through guide tube 70 as it is, and the position determining light is not reflected on guide tube 70.

On the other hand, when light is projected toward mark M, the measuring light passes through mark M as it is, and the position determining light is reflected by mark M and returns to light guide body 71 through prism 73 and light converging lens 72. The position determining light which has entered light guide body 71 again is split by coupler CB as shown in FIG. 1, is detected by photodetector for position determining light DB and is converted into synchronizing signal. In the structure of FIG. 3a, a unit of synchronizing signal is generated per one rotation of prism 73.

FIG. 3b shows an example that two marks M are formed in a scanning area of 360 degrees. The first and second marks M are arranged with an interval of 180 degrees. The first mark M is larger than the second mark M in width in order to distinguish the marks. When prism 73 rotates and light is projected toward first mark M, the measuring light passes through the mark M as it is, and the position determining light is reflected by the mark M and returns to light guide body 71. Then, first synchronizing signal is generated. When light is projected toward second mark M, the measuring light passes through the mark M as it is, and the position determining light is reflected by the mark M and returns to light guide body 71. Then, second synchronizing signal is generated. Thereby, two units of synchronizing signal are generated per one rotation of prism 73. Generally, when N marks M are arranged at intervals of 360/N degrees, N units of synchronizing signal are generated per one rotation of prism 73.

The probe relating to the present invention is suitable for a rotary scanning probe. As for a rotary scanning probe, a scanning area is continuous and a mark is hardly set outside the scanning area Therefore, it has been difficult to avoid that an image lacks because of the mark in the prior art. Further, the probe is suitable for a method that a rotating drive is carried out at the base of the probe in a rotary scanning probe. When a twist is generated in the method that a rotating drive is positioned at the base of the probe, the rotation at the drive section and the rotation condition at the leading end section sometimes do not agree with each other completely. Therefore, the present invention is suitable for that, because the rotation condition at the leading end section can be directly measured.

Plural marks M may be arranged along the longitudinal direction of guide tube 70, as shown in FIG. 2. In some conditions of measurement, light guide body 71 moves along the longitudinal direction with guide tube 70 being fixed. When light is projected toward mark M, the position determining light is reflected by mark M and returns to light guide body 71. Then, a unit of synchronizing signal is generated. After that, the total units of the synchronizing signal generated corresponding to the movement of light guide body 71 are counted, which enables to measure the displacement amount of light guide body 71.

Accordingly, when mark M is arranged on the side surface of light guide body 70, where the mark M has characteristics of transmitting the measurement light and returns only the position determining light to light guide body 71, the rotation angle and/or displacement amount of light guide body 71 can be measured by using the position determining light without affecting an observed image which is observed by using the measuring light.

Figure 4:
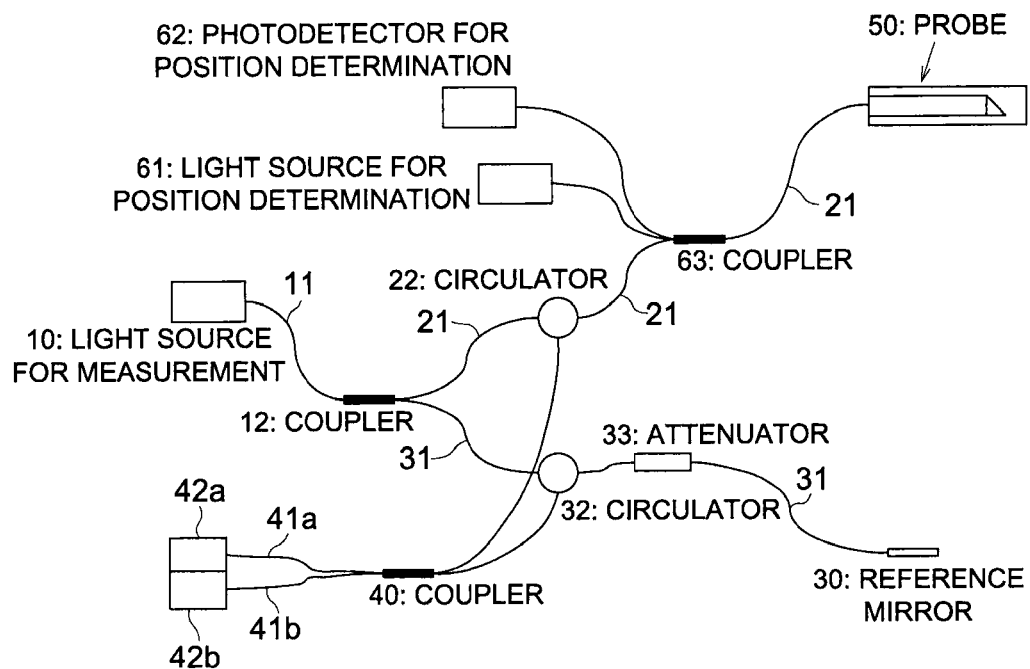
FIG. 4 is a structural view showing an example that an optical probe relating to the present invention is applied to an optical tomography measurement device.

FIG. 4 is a structural view showing an example that an optical probe relating to the present invention is applied to an optical tomography measurement device. The optical tomography measurement device is structured as a Michelson interferometer employing a low coherence light source. The optical tomography measurement device is composed of measurement light source 10, coupler 12, circulators 22, 32, attenuator 33, probe 50, reference mirror 30, coupler 40, differential detectors 42a, 42b, plural optical paths 11, 21, 31, 41a, 41b, and is additionally composed of light source for position determination 61, photodetector for position determination 62 and coupler 63 in order to use the position determining light by introducing the position determining light into the same optical path for the measuring light. Optical paths 11, 21, 31, 41a, 41b include flexible single-mode optical fibers.

Light source for measurement 10 includes an element such as SLD (Super Luminescent Diode), and generates low-coherence light, for example, whose central wavelength is 1.3 μm and spectral width of oscillation is about 50 nm. The measurement light from light source for measurement 10 passes through optical path 11 and reaches coupler 12.

Coupler 12 includes an element such as an optical fiber coupler and beam splitter, and has a function as a light splitting means which splits light from optical path 11 into branches in the predetermined ratio for optical paths 21 and 31.

The measuring light split by coupler 12 passes through optical path 21, circulator 22 and coupler 63 and reaches probe 50. Probe 50 irradiates the subject to be measured with the measuring light. The back measuring light which has been reflected corresponding to the internal structure of the subject to be measured, enters probe 50 again, goes back through optical path 21, and reaches coupler 40 through circulator 22.

The reference light split by coupler 12 passes through optical path 31, circulator 32 and attenuator 33 and reaches reference mirror 30. The back reference light which has been reflected by reference mirror 30 goes back through optical path 31, passes through attenuator 33 and circulator 32, and reaches coupler 40.

The back measuring light and back reference light go back through optical paths 21 and 31, respectively, and are mixed by coupler 40. Then, interfering light is generated. Coupler 40 includes an element such as an optical fiber coupler and a beam splitter and has a function as light interfering means which causes interference of light going back the optical paths 21 and 31. The interfering light passes through optical paths 41a and 41b and reaches differential detectors 42a and 42b, respectively. Differential detectors 42a and 42b output the difference of two interfering signals.

Various noise rejections and various filtering processing are performed for the signal from differential detectors 42a and 42b, and the resulting signal is converted into digital signal. After that, the signal is stored in a signal processing device such as a personal computer. The signal processing device constructs an optical tomographic image from the stored data, according to the method of optical tomography measurement which will be described later.

The method of the optical tomography measurement is roughly categorized into a time-domain OCT (TD-OCT) and a Fourier-domain OCT (FD-OCT), and the Fourier-domain OCT is further categorized into a swept-source OCT (SS-OCT) and a spectral-domain OCT (SD-OCT). In the time-domain OCT, one or more of optical phase modulators are arranged on one or both of optical path 21 and optical path 31, to modulate the phase of light corresponding to scanning signal. In the swept source OCT, a wavelength-variable light source is employed as light source 10 and wavelength of light is modulated corresponding to scanning signal. In the spectral-domain OCT, interfering light of the back measuring light and back reference light is separated into its spectral components with a grating and the resulting optical spectrum is measured with a linear image sensor.

The present invention can be applied to any one of the above methods, but the swept-source OCT and the spectral-domain OCT are preferable because no structure which changes the optical path length in terms of time is required in the optical path for the reference light.

According to the present embodiment, when differential detection is performed for the interfering signal of the back measuring light and the back reference light, the signal intensity is enlarged by the differential detection, because the signal obtained after light from the optical path for the measuring light and light from the optical path for the reference light interfere with each other becomes signal with the opposite phase. On the other hand, for example, the interfering signal caused by ghost generated on the optical surface of a prism arranged in the optical path for the measuring light is just divided in coupler 40 and has the same phase. Therefore, noise signal can be reduced by the differential detection, which allows obtaining an excellent tomographic image.

Further, there is provided a structure that the measuring light and the reference light are delivered by separate optical fibers, which enables to insert attenuator 33 only in the optical path 31 for the reference light. Thereby, the control of light amount of the back reference light can be realized easily and the light-mount adjustment suitable for the interference is performed. Further, because the measuring light and reference light pass through separate optical paths, ghost light which is caused in the optical path for the measuring light can be eliminated.

In the present embodiment, the position determining light from light source for position determination 61 is introduced through coupler 63 into optical path 21. When probe 50 performs rotary scanning and/or linear movement, the position determining light is reflected by mark M, enters probe 50 again, passes through coupler 63 and is detected by photodetector for position determination 62 as shown in FIG. 2 and FIGS. 3a and 3b. Then, synchronizing signal is generated. By using the synchronizing signal, the rotation angle and/or displacement amount of probe 50 can be measured. At that time, since mark M is transparent with respect to the measuring light, an image which is observed by using the measuring light does not lack and tomographic images can be obtain throughout the rotary scanning angle of 360 degrees In the present embodiment, the light guide body rotates on the axis, but the present invention can be applied to a scanning system wherein a MEMS mirror is arranged on the leading end of the probe and a system wherein a fiber itself is oscillated for scanning. In the systems, the scanning position on the leading end of the probe can be determined without attenuation of the measuring light, which allows obtaining an excellent OCT image.

INDUSTRIAL APPLICABILITY

The present invention is extremely useful industrially in the point that an optical characteristic measuring probe which can detect the position and direction of the leading end of the probe without affecting the observed image can be provided.

REFERENCE SIGNS LIST

10 Light source for measurement
11, 21, 31, 41a, 41b Optical path
12, 40, 63 Coupler
22, 32 Circulator
33 Attenuator
42a, 42b Differential detector
50 Probe
61 Light source for position determination
62 Photodetector for position determination
70 Guide tube
71 Light guide body
72 Light converging lens
73 Prism
M Mark

The invention claimed is:

1. An optical characteristic measuring device comprising:
   an optical characteristic measuring probe which is bendable, comprising a light guide body and a guide tube for holding the light guide body such that the light guide body freely rotates on an axis of the guide tube and is freely displaced in a direction of the axis;
   a measurement light source which supplies measuring light for measuring optical characteristic of a subject to be measured to the light guide body of the optical characteristic measuring probe; and
   a position determination light source which supplies position determining light for measuring a position of the light guide body to the light guide body of the optical characteristic measuring probe,
   wherein the light guide body guides the light from the measuring light source to the subject to be measured and guides the light from the position determination light source to the guide tube; and
   wherein the guide tube is provided with a mark arranged on a side surface of the guide tube, where the mark has a characteristic of transmitting the measuring light and returning only the position determining light to the light guide body.

2. The optical characteristic measuring device of claim 1, wherein the mark comprises a film having a reflectance which changes depending on wavelength and reflects light with a wavelength of the position determining light and transmits light with a wavelength of the measuring light.

3. The optical characteristic measuring device of claim 1, wherein the mark comprises a reflective volume grating which transmit infrared light and reflects visible light.

4. A method of measuring optical characteristic of a subject to be measured using an optical characteristic measuring probe which is bendable, the method comprising:
   guiding measuring light from a measurement light source to the subject to be measured through a light guide body of the optical characteristic measuring probe;
   guiding position determining light from a position determination light source to a mark arranged on a side surface of a guide tube of the optical characteristic measuring probe which holds the light guide body such that the light guide body freely rotates on an axis of the guide tube and freely displace in a direction of the axis, wherein the mark has a characteristic of transmitting the measuring light and returning the position determining light to the light guide body;
   detecting the measuring light reflected on the subject to be measured by a photodetector for measuring light; and
   detecting the position determining light reflected on the mark by a photodetector for position determining light.

5. The method of measuring optical characteristic of claim 4, wherein the mark comprises a film having a reflectance which changes depending on wavelength and reflects light with a wavelength of the position determining light and transmits light with wavelength of the measuring light.

6. The method of measuring optical characteristic of claim 4, wherein the mark comprises a reflective volume grating which transmit infrared light and reflects visible light.

* * * * *